United States Patent [19]

Zehner et al.

[11] Patent Number: 5,447,917
[45] Date of Patent: Sep. 5, 1995

[54] D-TAGATOSE AS ANTI-HYPERGLYCEMIC AGENT

[75] Inventors: Lee R. Zehner, Brookeville; Gilbert V. Levin, Annapolis; James P. Saunders, Rockville; James R. Beadle, Elkridge, all of Md.

[73] Assignee: Biospherics Incorporated, Beltsville, Md.

[21] Appl. No.: 190,938

[22] Filed: Feb. 3, 1994

Related U.S. Application Data

[63] Continuation of Ser. No. 835,496, Feb. 14, 1992, Pat. No. 5,356,879.

[51] Int. Cl.⁶ ............................................. A61K 31/70
[52] U.S. Cl. ...................................... 514/23; 514/866
[58] Field of Search ................................. 514/23, 866

[56] References Cited

U.S. PATENT DOCUMENTS

| | | | |
|---|---|---|---|
| 4,786,722 | 11/1988 | Zehner | 536/1.1 |
| 5,041,541 | 8/1991 | Mazur | 536/11 |
| 5,064,672 | 11/1991 | Mazur | 426/531 |
| 5,106,967 | 4/1992 | Mazur | 536/119 |

OTHER PUBLICATIONS

N. B. Ruderman, A. McCall, pp. 778–797, Medicine, Eds. R. W. Wilkins, N. G. Levinsky, Little Brown Co. Boston 1983.
A. Cerami et al., Glucose and Aging, Scientific American vol. 256, pp. 90–96, 1987.
A. Cerami, J. Am. Geriatr. Soc., vol. 33, pp. 626–634, 1985.
H. F. Bunn et al. Reaction of Monosaccharides Science, vol. 213, pp. 222–224, 1981.
G-J. Wolff et al. Chemie Zeitung vol. 103, pp. 232–233 1979.

Primary Examiner—Douglas W. Robinson
Assistant Examiner—Kathleen Kahler Fonda
Attorney, Agent, or Firm—William S. Ramsey

[57] ABSTRACT

This invention discloses edible formulations and pharmaceutical compositions containing D-tagatose and the effect of consumption of such formulations on blood level of glucose. D-Tagatose was found to be an anti-hyperglycemic agent. In addition, consumption of D-tagatose in sweetened formulations to inhibit formation of advanced glycosylation end-products in mammals is disclosed. The combination of the anti-hyperglycemic effect and the inhibition of formation of glycosylated proteins and nucleic acids make D-tagatose an ideal agent for alleviating the complications resulting from hyperglycemia, including acceleration of the aging process.

3 Claims, 2 Drawing Sheets

D-TAGATOSE AS ANTI-HYPERGLYCEMIC AGENT

This is a continuation of application Ser. No. 07/835,496 filed Feb. 14, 1992, now U.S. Pat. No. 5,356,8789.

BACKGROUND OF THE INVENTION

1. Field of the Invention

This invention relates to formulations which relieve hyperglycemia, control blood insulin, and obviate the consequential complications associated with diabetes mellitus and advanced aging, and describes methods for their use.

2. Description of the Related Art

Nonpregnant human adults with a fasting glucose concentration in venous plasma greater than 115 mg/dl are, by definition, hyperglycemic. (Neil B. Ruderman and Anthony McCall, Disorders of Carbohydrate Metabolism, pages 778–797, In *Medicine*, Eds. Robert W. Wilkins and Norman G. Levinsky, Little Brown and Company, Boston, 1983). Hyperglycemia is associated with diabetes mellitus, impaired glucose tolerance, and gestational diabetes. Persons with blood glucose concentrations greater than 115 but less than 140 mg/dl have impaired glucose tolerance (glucose intolerant). Persons with greater than 140 mg/dl blood glucose are regarded as diabetic.

Diabetes mellitus (DM) is defined as a group of disorders characterized by a relative or absolute lack of insulin and the presence of hyperglycemia. DM occurs in the following categories: type I or insulin-dependent DM; type II or noninsul-independent DM; nonobese DM; obese DM; maturity-onset diabetes of the young; and other types, including diabetes associated with certain conditions or syndromes.

The well-known acute and chronic complications of diabetes mellitus include diabetic ketoacidosis and hyperosmolar coma. In the absence of treatment, patients with DM die within 2 to 3 years of onset of the disease. The most important chronic complication of DM results from pathologic alteration in large and small blood vessels and in the nervous system. Such complications take the form of atherosclerosis, capillary angiopathy, and diabetic cardiopathy. Blindness, renal failure, gangrene, heart disease, peripheral neuropathy, and mononeuropathy may result. All of the above complications are likely a result of extensive glycosylation of proteins by the abnormally high concentration of glucose in blood and other tissues.

Some glucose intolerant persons develop type I or II DM. Glucose intolerance sometimes appears with pregnancy and is called gestational diabetes. Glucose intolerant persons have increased risk of atherosclerotic cardiovascular disease and greater risk of perinatal morbidity when pregnant. Patients with impaired glucose tolerance are often obese. Treatment is based on diet, exercise, and removal of drugs or other factors which may cause this condition.

Treatment of conditions involving hyperglycemia include diet. The diet for hyperglycemic persons is often comprised of 50% carbohydrate (primarily complex carbohydrates), not greater than 30% fat, and the remainder protein. Sugars such as sucrose and glucose are restricted because they elevate blood sugar levels. As a result, poor compliance with such diets is common. Sweeteners which do not elevate blood glucose levels are being sought for use in such diets to enhance compliance.

U.S. Pat. No. 4,786,722 discloses edible formulations and methods for preparation of edible formulations in which D-tagatose is used as a low-calorie carbohydrate sweetener and bulking agent. In this patent, D-tagatose was described as useful in foodstuffs and other edible formulations for people whose metabolizable carbohydrate intake must be restricted because of conditions such as diabetes mellitus or obesity.

SUMMARY OF THE INVENTION

We have now found that, in addition to its providing zero retained calories, D-tagatose has a blood glucose lowering or anti-hyperglycemic effect when ingested. Both the blood glucose level and the blood insulin demand associated with ingestion of common metabolizable sugars are moderated when D-tagatose is administered. This finding makes D-tagatose an anti-hyperglycemic agent and may be useful in foodstuffs and other edible formulations for people afflicted with hyperglycemia. Furthermore, ingestion of D-tagatose results in the reduced formation of advanced glycosylated end-products, which cause complications of hyperglycemia. As a result of the anti-hyperglycemic effect and the inhibition of advanced glycoslyated end-product formation, D-tagatose is useful for treatment of diabetes mellitus.

BRIEF DESCRIPTIONS OF FIGS. 1 & 2

DESCRIPTION OF PREFERRED EMBODIMENTS

U.S. Pat. No. 4,786,722, incorporated herein by reference, discloses edible formulations in which the low-calorie sweetening agent is D-tagatose. D-Tagatose is useful for sweetening all types of materials intended for consumption or contact with the mouth of the user.

EXAMPLE 1

Figure 1:
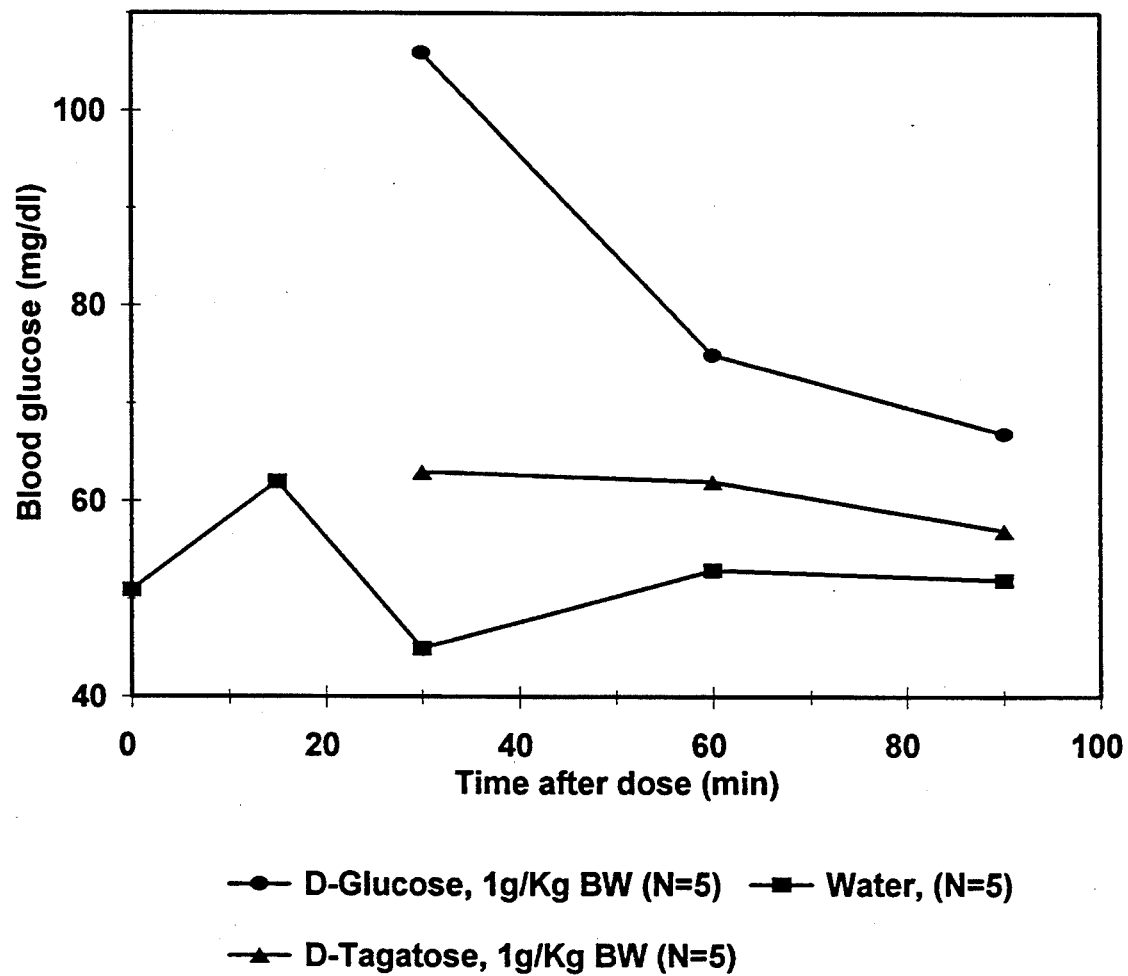
FIG. 1 is a graph showing the effect of orally ingested D-tagatose and D-glucose on rat blood glucose levels.
Figure 2:
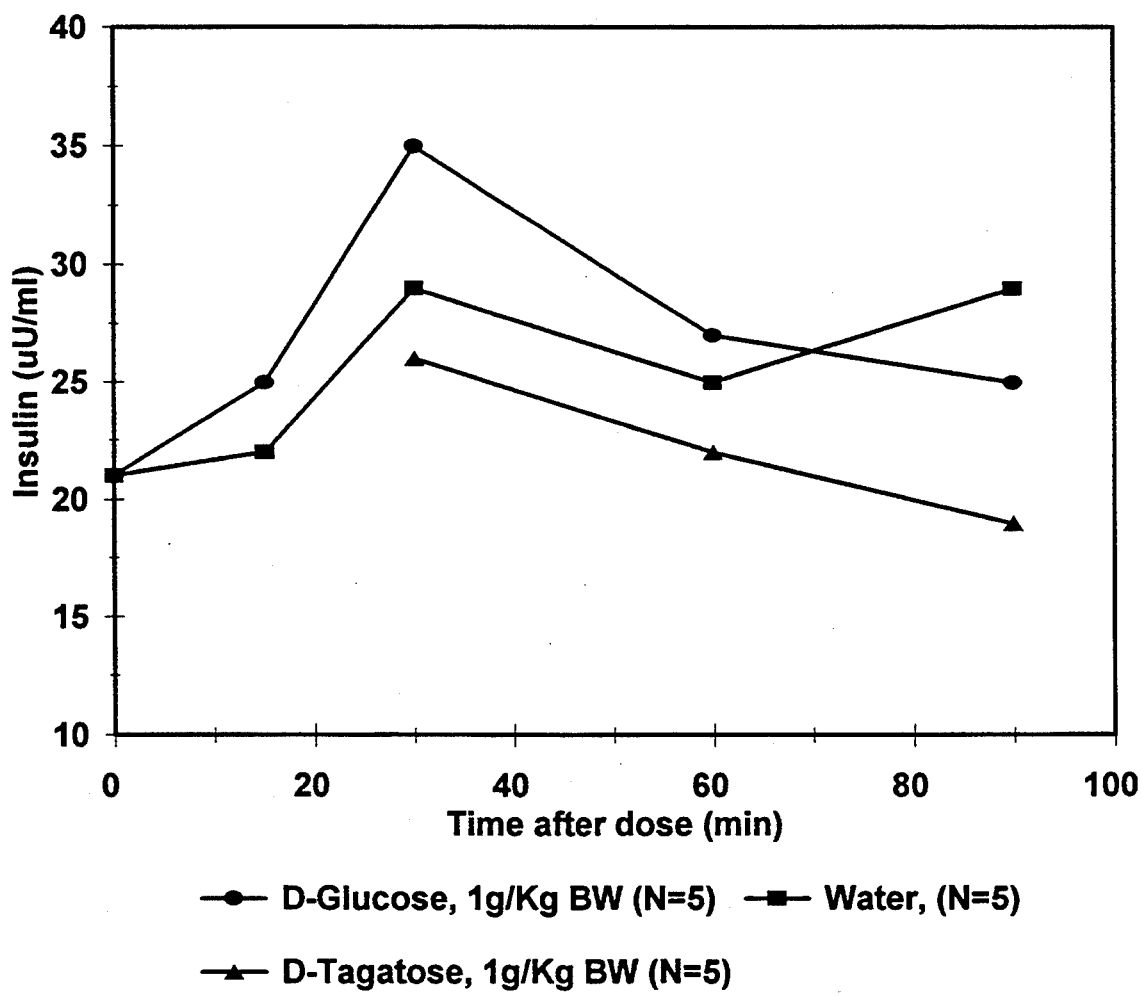
FIG. 2 is a graph showing the effect of orally ingested D-tagatose and D-glucose on rat blood insulin levels.

The effects of D-tagatose and D-glucose on the blood glucose and insulin levels in normal rats is shown in FIGS. 1 and 2. Five normal, healthy, fasting, 8-week old rats were administered by mouth a water solution of D-tagatose at a dose of 1 g D-tagatose per kg body weight (triangles). Mother set of five rats was administered by mouth a water solution of D-glucose at a dose of 1 g D-glucose per kg body weight (circles). A third set of five rats serving as controls received water only (squares). The blood levels of glucose and insulin were determined initially and at 30, 60, and 90 minutes after administration of the doses. The points show the average values of all 5 animals in each treatment group. The levels of blood glucose are indicated in mg glucose per dl blood in FIG. 1. The levels of blood insulin are indicated in $\mu$, U insulin per ml blood in FIG. 2.

END OF EXAMPLE 1

FIG. 2 shows that D-tagatose reduced the blood insulin demand in normal rats below the level after administration of D-glucose, and below the level in the control animals. Furthermore, when D-tagatose was administered, the blood insulin spike at 30 minutes associated with ingestion of common metabolizable sugars was less than that of the D-glucose dosed animals or of the control animals. D-Tagatose makes no insulin demand on animals. Little or no spike in blood glucose level was associated with D-tagatose ingestion (FIG. 1). The D-tagatose animals' blood glucose levels, while slightly above those of the control animals, were in every case below those of the D-glucose treated animals. D-Tagatose had an unexpected blood glucose lowering, or anti-hyperglycemic, effect. Again, this relieves the requirement for insulin.

Edible formulations in which the sweetening agent is D-tagatose may be consumed by humans with hyperglycemia who wish to avoid the increase in blood glucose associated with the consumption of common metabolizable sugars. D-Tagatose, in unit dosage if desired, and combined with pharmaceutically acceptable carriers if desired, also may be used to treat hyperglycemia and diabetes mellitus. Similar preparations may be used to lower blood insulin in humans requiring such a treatment.

Sugars in the blood react with proteins and nucleic acids and are thought to cause complications associated with diabetes and with aging (Anthony Cerami, Helen Vlassara, and Michael Brownlee, Glucose and Aging, Scientific American, 256 (5), pp. 90–96, 1987). In these reactions, the carbonyl carbon of a monosaccharide in the straight or open chain structure forms a Schiff base with an amine group on a protein or nucleic acid. The Schiff base then forms an Amadori product containing a carbonyl carbon, which reacts further with other molecules to form complex irreversible structures termed advanced glycosylation end-products. Such structures accumulate with age and are thought to inhibit normal protein and nucleic acid functions such as enzymatic activity, genetic expression, and binding of regulatory molecules (A. Cerami, J. Am. Geriatr. Soc., 33, pp. 626–634, 1985).

The reaction rate of a monosaccharide with hemoglobin to produce a glycoslated protein is dependent on the monosaccharide structure (H. Franklin Bunn and Paul J. Higgins, Reaction of Monosaccharides with Proteins: Possible Evolutionary Significance, Science, 213, pp. 222–224, 1981). The rate of reaction was found to correlate strongly with the extent to which the monosaccharide was in the open chain structure, as opposed to the ring structure. The % carbonyl, which indicates the fraction of open chain structure, was reported for D-glucose at 0.002%; for D-tagatose at 0.6%; and for D-fructose at 0.7%. Others reported the % keto for D-fructose at 0.80%; and for D-tagatose at 0.30% (Gerd-Joachim Wolff and Eberhard Breitmaier, $^{13}$C-NMR-spektroskopische bestimmung der keto-form in wassrigen losungen der D-fructose, L-sorbose und D-tagatose, Chemie Zeitung 103 (6), pp. 232–233, 1979). The rates of reactivity of monosaccharides with hemoglobin were: D-glucose, $0.60 \pm 0.07 \times 10^{-3}$ mM$^{-1}$ hr$^{-1}$; D-tagatose, $0.3 \times 10^{-3}$ mM$^{-1}$ hr$^{-1}$; and D-fructose $4.5 \times 10^{-3}$ mM$^{-1}$hr$^{-1}$. Thus D-tagatose had a lower reactivity with hemoglobin than did D-glucose or D-fructose. This lower reactivity of D-tagatose may be due in part to the lower concentration of straight chain structure relative to other ketoses and in part due to the lower reactivity of ketoses vs. aldoses, which are less sterically hindered (more reactive molecules) than ketoses.

EXAMPLE 2

Five 6-week old Sprague-Dawley male rats are fed ad libitum a nutritionally complete diet containing 15 wt % D-tagatose for 90 days. A control set of rats are fed a diet differing only in that sucrose is substituted for D-tagatose for 90 days. Examination of the blood, dura mater, and collagen in blood vessels of each set of rats indicates a higher level of advanced glycosylation end-products in the rats fed sucrose than in the rats fed D-tagatose.

END OF EXAMPLE 2

The consumption of sweetened edible formulations in which D-tagatose is the sweetening agent therefore results in a lower rate of formation of advanced glycosylation end-products than would consumption of similar formulations sweetened with D-glucose or D-fructose, or sweetened with sweeteners such as sucrose, which are hydrolyzed by the body to D-glucose and D-fructose as intermediate metabolites. D-Tagatose may also be administered in unit dosage form to humans to reduce the rate of formation of advanced glycosylation end-products. The lower rate of formation of advanced glycosylation end-products will prevent the complications of diabetes mellitus described above, and may have other beneficial effects in humans.

The above discussion is primarily directed to preferred embodiments and processes. It will be readily apparent to those skilled in the art that further changes and modifications can be made without departing from the scope of the invention as defined in the following claims.

We claim:

1. A method for treating diabetes by inhibiting the rise in blood sugar associated with the consumption of sugar by a mammal in need of such treatment consisting of administering to said mammal an amount of D-tagatose effective in inhibiting the rise in blood sugar associated with the consumption of sugar.

2. The method of claim 1 wherein the amount of D-tagatose administered is 1 g per kg of weight of the mammal.

3. The method of claim 1 wherein the mammal is a human.

* * * * *